United States Patent
McGee et al.

(10) Patent No.: US 6,803,033 B2
(45) Date of Patent: Oct. 12, 2004

(54) PROCESS FOR MAINTAINING FRAGRANCE PERCEPTION IN THE PRESENCE OF AN ABSORBENT MATERIAL

(75) Inventors: Thomas McGee, Nanuet, NY (US); Kenneth Leo Purzycki, Lake Parsippany, NJ (US); Richard P. Sgaramella, Hoboken, NJ (US)

(73) Assignee: Givaudan SA, Geneva (CH)

( * ) Notice: Subject to any disclaimer, the term of this patent is extended or adjusted under 35 U.S.C. 154(b) by 0 days.

(21) Appl. No.: 10/295,630

(22) Filed: Nov. 15, 2002

(65) Prior Publication Data

US 2003/0072733 A1 Apr. 17, 2003

Related U.S. Application Data

(63) Continuation of application No. 09/668,873, filed on Sep. 25, 2000, now abandoned.

(51) Int. Cl.[7] ............................................... A61L 9/00
(52) U.S. Cl. ..................................... 424/76.1; 424/489
(58) Field of Search .............................. 424/489, 484, 424/490, 76.1, 76.4, 400, 404

(56) References Cited

U.S. PATENT DOCUMENTS

| | | | | |
|---|---|---|---|---|
| 5,295,456 A | * | 3/1994 | Lawson | 119/172 |
| 5,429,628 A | | 7/1995 | Trinh | 604/359 |
| 5,489,469 A | * | 2/1996 | Kobayashi et al. | 442/393 |
| 5,582,603 A | * | 12/1996 | Difilippantonio et al. | 604/380 |
| 5,733,272 A | * | 3/1998 | Brunner et al. | 604/359 |
| 5,962,106 A | * | 10/1999 | De Carvalho et al. | 428/131 |
| 6,203,810 B1 | * | 3/2001 | Alemany et al. | 424/404 |
| 6,221,826 B1 | * | 4/2001 | Surutzidis et al. | 510/349 |
| 6,245,732 B1 | * | 6/2001 | Gallon et al. | 510/507 |

FOREIGN PATENT DOCUMENTS

| | | |
|---|---|---|
| EP | 0 816 484 A2 | 1/1998 |
| EP | 1 061 124 A1 | 12/2000 |
| WO | 94 22500 A | 10/1994 |
| WO | 98 26808 | 6/1998 |
| WO | 99 04830 | 2/1999 |

OTHER PUBLICATIONS

European Search Report, dated Dec. 9, 2002, for EP 01 12 2346.

* cited by examiner

*Primary Examiner*—Thurman K. Page
*Assistant Examiner*—Robert M. Joynes
(74) *Attorney, Agent, or Firm*—Norris McLaughlin & Marcus PA

(57) ABSTRACT

A process is provided for absorbing moisture and/or malodor and providing a fragrance to the surrounding ambience that includes providing a delivery vehicle containing an enrobement material, a fragrance, and a fixative, combining the delivery vehicle with an absorbent material, and contacting the mixture of delivery vehicle and absorbent material with moisture and/or a malodor source.

34 Claims, No Drawings

PROCESS FOR MAINTAINING FRAGRANCE PERCEPTION IN THE PRESENCE OF AN ABSORBENT MATERIAL

This application is a continuation application of U.S. Ser. No. 09/668.873, filed Sep. 25, 2000 now abandoned.

FIELD OF THE INVENTION

The present invention relates to a process for releasing fragrance in the presence of absorbent materials. More particularly, the process includes providing a delivery vehicle containing an enrobement material, a fragrance, and a fixative, which are then combined with a moisture and/or malodor absorber to convey a fragrance to the atmosphere, and to provide an absorbent for moisture and/or malodors.

BACKGROUND OF THE INVENTION

Absorbent materials are well known in the art to absorb moisture or malodors in products such as sanitary products, diapers, cat litter, air fresheners, and the like. Often mixtures of absorbents are used to obtain optimum performance with good odor control. For example, Brewer, U.S. Pat. No. 3,789,797 discloses an animal litter prepared from alfalfa, bentonite, and a binder for absorbing and neutralizing the odors of animal waste matter. Dickey, U.S. Pat. No. 4,519,340 discloses an absorbent composition for absorbing animal waste made from a mixture of natural absorbents such as corn stalks, wood shavings, hulls of cereal grain, and other components. Goodwin et al., U.S. Pat. No. 4,571,389 discloses an absorbent based on rice hull ash with multiabsorbent purposes. Karapasha et al., U.S. Pat. No. 5,306,487 discloses a particle composition for use with diapers and the like, which is based upon a high absorbent gelling material combined with odor-controlling materials such as zeolites, for example molecular sieve zeolites marketed under the trade name of ABSCENTS (Union Carbide Corporation and UOP), and activated carbon. Guarracino et al., U.S. Pat. No. 6,096,299 discloses an odor control material based upon a zeolite with a specific particle size. Neckernann, U.S. Pat. No. 3,816,577 discloses a cherry pit extract for deodorizing animal waste.

In absorbent products, it is also desirable to release a deodorant or a masking scent to maintain a pleasant smelling environment. In such products, fragrances are normally added directly to a particulate material or pre-mixed into an absorbent carrier. It is recognized that absorbers, especially those with high odor absorption capacity, may reduce the impact of fragrances if the fragrance is added directly to the absorber or premixed with, e.g., a zeolite.

For example, Kiebke, U.S. Pat. Nos. 5,216,980, and 5,361,719 each disclose a composition in which the fragrance carrier is ground corncob. Brewer, U.S. Pat. No. 3,921,581 discloses a moisture sensitive fragrance releasing solid containing powdered solids, such as finely ground alfalfa and sawdust with pre-gelatinized starch as the moisture sensitive ingredient. Miller, U.S. Pat. No. 3,675,625 discloses that when fragrance is added to absorbent material, it is no longer easily perceived until desorbed by moisture. In this composition, moisture release overcomes some of the problems but because the bulk absorber is hydrophilic, fragrance release is of short duration and malodors may be perceived if the absorber has only moderate odor absorbing capacity. The use of a high malodor absorbent capacity powder in such a system reduces both the malodor and the scent. For example, Paul, U.S. Pat. No. 5,782,409 discloses an air freshening and deodorizing system in which the fragrance and the malodor absorber are kept physically separated to overcome this problem.

In sum, heretofore when a fragrance was combined in a malodor/moisture absorbing system, an undesirable loss of fragrance or reduction in fragrance longevity was observed. This effect was even more pronounced when a super absorbent material was combined with such systems. As noted above, to combat this problem, the fragrance component was maintained separately from the absorbent material. The requirement for such separation, however, was inconvenient, uneconomical, and inefficient.

SUMMARY OF THE INVENTION

Thus, a need exists for a process for absorbing moisture and/or malodor, and providing a scent to the surrounding ambience (air) that avoids the problems of the prior art summarized above. Preferably, the process should be easy to use by the consumer, and utilize a composition that does not require that the fragrance and the absorbent material, e.g., moisture and/or malodor absorber, be physically separated.

One embodiment of the invention is a process for absorbing moisture and/or malodor, and providing a fragrance to the surrounding ambience. This process includes (a) providing a delivery vehicle containing an enrobement material, a fragrance, and a fixative, wherein the delivery vehicle is a free flowing powder; (b) combining the delivery vehicle with an absorbent material to form a mixture; and (c) contacting the mixture of (a) and (b) with a moisture and/or a malodor source.

Another embodiment of the invention is a fragranced delivery vehicle. This fragranced delivery vehicle includes a fragrance composition dispersed in a fixative and an enrobement material, wherein the fragrance composition, fixative, and enrobement material, when combined, form a free flowing powder.

Another embodiment of the invention is a process for providing a fragrance and moisture and/or malodor absorbing capacity to a substrate. This process includes (a) providing a free flowing powder containing a fragrance composition, a fixative, an enrobement material, and an absorbent material; and (b) contacting the free flowing powder with the substrate.

Another embodiment of the invention is a composition for absorbing moisture and/or malodor and imparting a fragrance to a surrounding environment. This composition includes from about 30% (wt) to about 98% (wt) of an absorbent material; from about 1% (wt) to about 20% (wt) of a delivery vehicle, wherein the delivery vehicle includes, in a free flowing powder, a fragrance, a fixative, and an enrobement material; and 0% to 50% (wt) of fillers and binders.

A further embodiment of the invention is a fragrancing and moisture and/or malodor suppression system. This system includes (a) a free flowing powder containing a fragrance composition, a fixative, and an enrobement material combined with an absorbent material; (b) a housing means for housing the free flowing powder including the absorbent material; and (c) a vapor permeable outer material disposed about the housing means, wherein moisture and malodor from a surrounding environment may diffuse through the outer material and into the free flowing powder and fragrance from the free flowing powder may diffuse through the outer material into the surrounding environment.

DETAILED DESCRIPTION OF THE INVENTION

The present invention provides a low cost process for fragrancing the surrounding ambience (i.e., air) and absorbing moisture and/or malodor. The process includes providing a delivery vehicle containing an enrobement material, a fragrance, and a fixative, wherein the delivery vehicle is a free-flowing powder. The delivery vehicle is combined with an absorbent material, and then contacted with moisture and/or malodor.

In the present invention, the phrase "delivery vehicle" means a fragrance material, such as a perfume, sequestered in a protective matrix to minimize contact with the absorbent material. In this process, the delivery vehicle is in the form of a free flowing powder, and is mixed directly with an absorbent material, such as a moisture absorber, which optionally has a high malodor absorber capacity or has a material in it to enhance the malodor absorption capacity. As used herein, the terms "absorbent," "absorber," and "absorbent material" are used interchangeably, and refer to the same materials.

In the present invention, the delivery vehicle is composed of a fixative and a fragrance that is enrobed in enrobement materials, i.e., powder materials that are capable of absorbing oleophilic fragrance materials to such an extent that the resultant mixture is a free flowing powder. In the present invention, the enrobement materials include for example, clays; silicas; celites; zeolites; metal salts, including for example, phosphates; cellulose, such as methyl cellulose; starches, carbonates, such as sodium bicarbonate; borates, such as sodium borate; sulfates such as sodium sulfate; water soluble polymers, borax; and mixtures thereof.

For purposes of the present invention, a composition is considered to be a free-flowing powder if 500 grams of the composition are placed into a one liter glass beaker and left overnight, and that composition, when the beaker is slowly tilted, is dispensed without having to mechanically dislodge it from the beaker. Moderate and 95% free flowing powder compositions may also be used in the present invention. (See Example 5)

In the present invention, the fixative is a high molecular weight, low melting wax or solid that may be mixed readily with the free flowing powder. Examples of suitable fixatives for use in the present invention include polyethylene glycol, glycerol, mineral oil, and mixture thereof. The molecular weight of the fixative in the present invention may vary between about 400 Daltons to about 20,000 Daltons, preferably between about 2,000 Daltons to 10,000 Daltons. Other fixatives having a similar viscosity and melting point to polyethylene glycol are also contemplated by the present invention.

In the present invention, the fragrance is a mixture of fragrance materials selected from such classes as acids, esters, alcohols, aldehydes, ketones, lactones, nitriles, and hydrocarbons. Such fragrance materials are described, for example, in S. Arctander Perfume Flavors and Chemicals Vols. 1 and 2, Arctander, N.J. USA. The fragrance may optionally have aroma chemicals that are known to reduce the perception of malodors, such as for example, the materials disclosed by Kubelka, U.S. Pat. Nos. 3,074,849, 3,074, 892 and 3,077,547, and Schleppnik, U.S. Pat. Nos. 4,187, 251, 4,622,221 and 4,719,105, each of which are hereby incorporated by reference as if recited in full herein.

The ratio of the fragrance (i.e., perfume), enrobement materials, and fixative are carefully controlled in the present invention to ensure the powder is free flowing. Thus, in this invention, the ratio of fragrance-to-enrobement material is about 1:20 to about 2:5, preferably about 1:5, wherein the total amount of clay materials in the delivery vehicle composition are maintained below 50% (wt), preferably below 15% (wt).

One or more optional auxiliary agents may also be contained in the delivery vehicle or in the absorbent material. As used herein, an "auxiliary agent" is any composition that imparts a benefit to the free flowing powder. Such auxiliary agents may include, for example, flow aids, antimicrobial agents, pigments, dyes, surfactants, emulsifiers, binders, flow agents, enzyme inhibitors, antioxidants, insect repellents, insecticides, attractants, pH modifier, fillers, deodorants, and mixtures thereof.

In the present invention flow aids are ingredients that lessen or eliminate caking or stickiness of the powder, such as for example, hydrophobic silica and aluminosilicates.

In the present invention, the antimicrobial agents may include, for example, metal salts such as zinc citrate, zinc oxide, zinc pyrethiones, and octopirox; organic acids, such as sorbic acid, benzoic acid, and their salts; parabens, such as methyl paraben, propyl paraben, butyl paraben, ethyl paraben, isopropyl paraben, isobutyl paraben, benzyl paraben, and their salts; alcohols, such as benzyl alcohol, phenyl ethyl alcohol; boric acid; 2,4,4'-trichloro-2-hydroxy-diphenyl ether; phenolic compounds, such as phenol, 2-methyl phenol, 4-ethyl phenol; essential oils such as rosemary, thyme, lavender, eugenol, geranium, tea tree, clove, lemon grass, peppermint, or their active components such as anethole, thymol, eucalyptol, famesol, menthol, limonene, methyl salicylate, salicylic acid, terpineol, nerolidol, geraniol, and thereof.

In the present invention, it is preferred that about 10% (wt) to about 50% (wt) of the fragrance composition be incorporated into the delivery vehicle.

As used herein, "absorbent material" means any material that may absorb an aqueous liquid or a malodor ("malodor absorber") in sufficient quantities to provide dampness and/or malodor control. A material for absorbing an aqueous liquid is one that can absorb at least 50% by weight of water. Malodor absorbers are materials that reduce the perception of a malodor smell. For purposes of the present invention, a malodor absorber is identified by the following: 0.5 grams of the putative absorber is placed into a closed one liter vessel and 10 µl pyridine is introduced via a septum, and left to equilibrate at 25° C. for 15 minutes. If the amount of pyridine is reduced in the headspace by at least 5%, then material is considered to be a malodor absorber.

The absorbent materials according to the present invention include absorbent clays, such as diatomaceous earth, and Fuller's earth; bentonites, such as monmorillonite, kaolinite, hailosite, illite, and Georgia Clay; cellulosic derivatives, such as cellulose acetate, cellulose butyrate, cellulose proprionate; superabsorbents, including water swellable polymers, such as polysaccharides, polyacrylates, polyacylonitriles, polyvinyl alcohol, hydrophilic polyurethanes, partially hydrolyzed polyacrylamides, sulphonated polystyrene, sulphonated polyethers, and poly (alylene oxide); organic absorbents, such as ground corn cob, rice hull ash, ground alfalfa, cracked wheat, semolina, wood shavings, chopped soya bean stalk, peanut hull, hulls of cereal grain, and peat moss; and mixtures thereof.

In the present invention, malodor absorbers that are capable of absorbing significant quantities of gaseous malodors (i.e., high malodor absorbers) may also be incorporated into the free flowing powder. As used herein, high malodor absorbers are identified by the following: 0.5 grams of the absorber is placed into a closed one liter vessel and 10 ul pyridine is introduced via a septum, and left to equilibrate at 25° C. for 15 minutes. If the amount of pyridine is reduced in the headspace by at least 10%, preferably 20%, then the material is considered to be a high malodor absorber. Such high malodor absorbents may include inorganic absorbents, such as for example, molecular sieves, such as zeolites, silicas, aluminosilcates, cyclodextrins; and organic absorbents, such as for example, activated charcoal, dried citrus pulp, cherry pit extract, and mixtures thereof.

In the present invention, deodorant materials may also be incorporated into the free flowing powder. Such deodorant materials include, for example, chlorophyll, sodium dihydrogen phosphate, potassium acid phthalate, sodium bicarbonate, and mixtures thereof.

In the present invention, binders may also be added to the free flowing powder. As used herein, "binders" are materials that help form suitably sized particles, such as for example, particles having a diameter greater than 0.01 mm and less than 2 mm. Examples of binder material include starches, gums, glues, and mixtures thereof.

The free flowing powder may also include fillers. As used in the present invention, "fillers" are low absorbent materials used to bulk out the absorbent, such materials include, for example, cellulose, sand, soil, ground rock, fly ash, and mixtures thereof.

In the products produced according to the process of the present invention, when moisture or malodor comes into contact with the absorbent material in the free flowing powder, they are absorbed, and the fragrance in the delivery vehicle provides a fragrance ambience to the surrounding environment. The amount of the moisture and/or malodor to be absorbed depends upon the purpose of use. The amount and the type of absorbent incorporated into the free flowing powder is selected according to the requirements of use; the amount of fragrance released from the vehicle is likewise tailored to the specific use. The absorbent and fragranced delivery vehicles are mixed in proportions to achieve the desired results.

The moisture and/or malodor absorber will be present at about 30% (wt) to 98% (wt), high malodor absorbents will be present from about 0% (wt) to 30% (wt). In the present invention, combinations of absorbers may also be used with the delivery vehicle. The fragranced delivery vehicle will be present from about 1% (wt) to 20% (wt), and the fillers and optional ingredients will be present in the delivery vehicle at about 0% (wt) to 50% (wt).

The mixture of absorber and delivery vehicle according to the present invention may be loosely contained such as in a cat box, or held in a porous outer container, such as a woven or non-woven fabric. The outer container may be designed in any convenient shape, so long as moisture and malodor may enter the container, and the fragrance composition is releasable into the environment.

The delivery vehicles of the present invention may be used alone, or incorporated into, for example, cat litter, air fresheners, sanitary products, and diapers. As used herein, "sanitary products" include, for example, catamenials, panty liners, adult incontinence pads, underarm shields, shoe inserts, and the like. In addition, the delivery vehicle of the present invention may be incorporated into any product that is designed to absorb fluid and/or odors.

The delivery vehicle and/or products incorporating the delivery vehicle may be contained in any conventional housing (i.e., "housing means"), such as for example, cat litter boxes, plastic containers, compressed cardboard, and the like. Typical housings for sanitary- and air freshener-type products may be three-dimensional containers having a wall separating an inner space from an outer environment. The container may be made from natural, e.g. natural woven cotton, jute, and non-woven synthetics such as polyesters, propylene, viscose and blends of natural and synthetics. The shape of the housing is determined by the intended application; for example, the housing may be cylindrical, spherical, ellipsoidal, square, rectangular, or rectangular. The weight of the housing is also a function of the application. In general, the housing weight will range between about 5 grams to about 400 grams per square centimeter. The housing of the present invention is capable of transmitting liquids or vapors.

The following examples are provided to further illustrate the compositions and processes of the present invention. These examples are illustrative only and are not intended to limit the scope of the invention in any way.

EXAMPLES

Example 1

Fragranced Delivery Vehicle

Delivery Vehicle

A delivery vehicle was made by combining the following components:

TABLE 1

| Ingredient | | % (w/w) |
| --- | --- | --- |
| Fragrance | GJQ631AG3J | 30 |
| Fixative | Polyethylene Glycol 4000 | 1 |
| Clay | Bentonite | 9 |
| Zeolite | VALFOR 100 | 60 |

The fragrance was mixed into the fixative. The dry components (ie., clay and zeolite) were blended in a mixing vessel. Half of the liquid portion (i.e., fragrance/fixative mixture) was then added to the mixing vessel with stirring. The components were mixed until the liquid portion was well incorporated into the dry components. Then, the rest of the liquid portion was mixed until the composition was a free flowing powder.

Each of the absorbents listed in Table 2 below was tested with both neat fragrance and the fragrance in the delivery vehicle (fragranced delivery vehicle), respectively. 30 grams of each absorbent were placed into a 4-ounce jar. Into each absorbent, 3 grams of neat oil were dispersed for a concentration of 10% (wt). Into a second set of 30 gram absorbents, 10 grams of the fragranced delivery vehicle was mixed with the absorbent.

All of the samples were left exposed to the air for 30 minutes before evaluation by a five-member panel.

Each sample was coded prior to testing. Each panelist was asked to smell each pair of absorbent samples (Paired Comparison), and to select the one they felt had the strongest fragrance intensity.

TABLE 2

Fragrance Strength Comparison: Neat vs Fragranced Delivery Vehicle

| Absorbent | Neat | Delivery Vehicle |
| --- | --- | --- |
| Sodium Bicarbonate | 2/5 | 3/5 |
| Corn Cob | 1/5 | 4/5 |
| ABSCENTS | 1/5 | 4/5 |
| Cyclodextrins | 0/5 | 5/5 |
| Clay | 2/5 | 3/5 |
| Charcoal | 0/5 | 5/5 |

Example 2

Comparison Between Fragrance in Carrier and Delivery Vehicle

This experiment compared the fragrance intensity between a fragrance oil carried by a standard absorbent, such as zeolite, and a fragrance incorporated into a delivery vehicle of the present invention.

The following compositions were prepared in duplicate using fragrance formula GJQ631AGJ:

A. Zeolite+30(wt) % fragrance (Neat)

B. Delivery Vehicle of Example 1 (Table 1)

C. Zeolite+10(wt) % fragrance+corn cob absorbent base (Neat)

C. Delivery Vehicle (10(wt) %) of Example 1 (Table 1)+corn cob absorbent base

Each composition (i.e., Compositions A–D) were held in open jars at 70° C. for 4 hours, which conditions approximate certain conditions likely to be encountered during commercial manufacturing processes. The fragrance intensity of each composition was measured directly.

Each sample was coded prior to testing. A 15-member panel was asked to smell each pair of absorbent samples (Paired Comparison) and to select the one they felt had the strongest fragrance intensity.

TABLE 3

Fragrance Strength Comparison: Zeolite vs Delivery Vehicle

| Absorbent | Strength |
| --- | --- |
| Composition A | 3/15 |
| Composition B | 12/15 |
| Composition C | 5/15 |
| Composition D | 10/15 |

As Table 3 demonstrates, the fragrance oil when incorporated into the delivery vehicle of the present invention provides a significantly stronger fragrance signature compared to the Zeolite alone. A panel score of 12/15 (Composition B) is significant at the 95% confidence level for a paired comparison evaluation. The inclusion of a fixative in the delivery vehicle formulation clearly helps to protect the volatile oil during manufacture.

Table 3 also demonstrates that the superior fragrancing effects of using the delivery vehicle of the present invention containing a fragrance (Composition B) compared to the fragrance+zeolite carrier alone (Composition A) are also observed when the delivery vehicle including a fragrance is combined with an absorbent base, such as corncob (Composition D). A panel score of 10/15 is significant at the 90% confidence level for a paired comparison evaluation.

Thus, the use of an absorbent carrier, such as zeolite alone, is not sufficient to ensure a strong fragrance signature. Table 3 also demonstrates the clear benefit of the delivery vehicle of the present invention compared to zeolite carriers alone in terms of having a stronger fragrance impact, both neat (out of product) and in the presence of an absorbent, such as corncob.

Example 3

Delivery Vehicle Incorporated Into Cat Litter

The following cat litter formulations were prepared by combining, in a dry hopper, various cat litter substrates, absorbers, and a fragranced Delivery Vehicle prepared according to Example 1 (Table 1). Delivery Vehicles were prepared according to Example 1 (Table 1) containing 30% (wt) of a fragrance. The fragrance level in each formulation was 3% (wt).

| Formulation I | |
| --- | --- |
| Vermiculite (Mica) | 70 grams |
| Corn Cob | 20 grams |
| Delivery Vehicle (Ex. 1) (30% wt) | 10 grams |
| Formulation II | |
| Clay | 70 grams |
| Corn Cob | 20 grams |
| Delivery Vehicle (Ex. 1) (30% wt) | 10 grams |
| Formulation III | |
| Compacted Pine pellets | 70 grams |
| Zeolite (VALFOR-100-PQ Corp.) | 20 grams |
| Delivery Vehicle (Ex. 1) (30% wt) | 10 grams |
| Formulation IV | |
| Wood Shavings | 70 grams |
| Abscents (UOP Corp.) | 20 grams |
| Delivery Vehicle (Ex. 1) (30%) | 10 grams |

Example 4

Delivery Vehicle Incorporated Into Sachets

Various sachet formulations were prepared by mixing, in a dry hopper, the components set forth below. The various formulations were then evaluated for odor intensity. In these sachets, the fragrance level was 6% (wt). Using a 10-member panel, the fragrance intensity of each formulation was measured on a 5-point scale from 0–5, with a score of 5 being the highest odor intensity.

| | | Odor Intensity |
| --- | --- | --- |
| Formulation V | | 4 |
| Plastic Polymer beads (Polyvel Inc.) (Containing 3% wt fragrance in a polyethylene substrate) | 30 grams | |
| Zeolite (VALFOR-100-PQ Corp.) | 10 grams | |
| Delivery Vehicle (30% wt) (Ex. 1) | 10 grams | |
| Formulation VI | | 3.5 |
| Plastic Polymer beads (Polyvel, Inc.) (Containing 3% wt fragrance in a polyethlene substrate) | 30 grams | |
| Zeolite (VALFOR-100-PQ Corp.) | 10 grams | |
| Neat Fragrance | 1.5 grams | |
| Formulation VII | | 4 |
| Corn Cob | 40 grams | |
| Delivery Vehicle (30% wt) (Ex. 1) | 10 grams | |
| Formulation VIII | | 3.5 |
| Corn Cob | 40 grams | |
| Zeolite Carrier (VALFOR-100-PQ Corp.) + Fragrance (30% wt) | 10 grams | |
| Formulation IX | | 2.5 |
| Activated Charcoal | 40 grams | |
| Zeolite Carrier (VALFOR-100-PQ Corp.) + Fragranced Delivery Vehicle (Ex. 1) (containing 30% wt fragrance) | 10 grams | |
| Formulation X | | 2.0 |
| Activated Charcoal | 47 grams | |
| Neat Fragrance | 3 grams | |

Example 5

Powder Formulations

Powder formulations were evaluated for their flowability. 200 grams of each test blend ("formulation") were prepared, placed in a glass beaker, and left to stand overnight. The degree of flowability was measured as a function of how much residue remained in the beaker upon visual inspection after pouring out the contents.

|  | % wt | Flow Characteristics |
| --- | --- | --- |
| Formulation XI |  | Free Flowing |
| Fixative | 1 |  |
| Clay | 9 |  |
| Zeolite | 60 |  |
| Fragrance | 30 |  |
| Formulation XII |  | 95% Free Flowing |
| Fixative | 10 |  |
| Clay | 9 |  |
| Zeolite | 50 |  |
| Fragrance | 30 |  |
| Formulation XIII |  | Moderate Free Flowing |
| Fixative | 1 |  |
| Clay | 15 |  |
| Zeolite | 54 |  |
| Fragrance | 30 |  |
| Formulation XIV |  | Not Free Flowing |
| Fixative | 1 |  |
| Clay | 40 |  |
| Zeolite | 29 |  |
| Fragrance | 30 |  |

These data indicate that having high amounts of clay in the composition dramatically reduces the flow characteristics of the formulations.

Example 6

Fragrance Intensity in Catamenial Substrates

Catamenial substrates made from compressed cellulose fiber pads were combined with a zeolite carrier and a fragrance or with a zeolite and delivery vehicle according to Example 1 (Table 1). Both catamenial substrates were fragranced as set forth below. Six panelists were then asked to evaluate each catamenial substrate for fragrance intensity (Paired comparison). The results are presented below:

|  |  | Strength |
| --- | --- | --- |
| Catamenial Substrate 1 |  | 4/6 |
| Cellulose Fibers | 80% |  |
| Zeolite | 10% |  |
| Delivery Vehicle (Ex. 1) | 10% (30% Fragranced carrier) |  |
| Catamenial Substrate 1 |  | 2/6 |
| Cellulose Fibers | 85% |  |
| Zeolite | 12% |  |
| Neat Fragrance | 3% |  |

The data presented above indicate that using a fragranced delivery vehicle according to the present invention imparts significantly greater fragrance intensity to a catamenial substrate compared to the same substrate without the delivery vehicle (4/6 vs. 2/6).

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for absorbing moisture and/or malodor, and providing a fragrance to the surrounding ambience comprising:

(a) providing a delivery vehicle comprising an enrobement material, a fragrance, and a fixative, which is selected from the group consisting of polyethylene glycol, glycerol, mineral oil, and mixtures thereof, wherein the delivery vehicle is in the form of a free flowing powder, wherein the powder consists of a fragrance dispersed in the fixative, wherein the fragrance dispersed in the fixative is enrobed by the enrobement material, wherein the enrobement material is selected from the group consisting of clays, silicas, celites, zeolites, metal salts, celluloses, starches, carbonates, borates, sulfates, water soluble polymers, borax, and mixtures thereof;

(b) combining the delivery vehicle with an absorbent material to form a mixture; and (c) contacting the mixture of (a) and (b) with a moisture and/or a malodor source.

2. A process according to claim 1 wherein the molecular weight of the fixative is from about 400 Daltons to about 20,000 Daltons.

3. A process according to claim 2 wherein the molecular weight of the fixative is from about 2,000 Daltons to about 10,000 Daltons.

4. A process according to claim 1 wherein the absorbent material comprises a malodor absorber.

5. A process according to claim 4 wherein the malodor absorber is a high malodor absorbent selected from the group consisting of inorganic absorbents, molecular sieves, organic absorbents, and mixtures thereof.

6. A process according to claim 5 wherein the molecular sieve is selected from the group consisting of zeolites, silicas, aluminosilicates, cyclodextrins, and mixtures thereof.

7. A process according to claim 5 wherein the organic absorbent is selected from the group consisting of activated charcoal, dried citrus pulp, cherry pit extract, and mixtures thereof.

8. A process according to claim 1 wherein the absorbent material is an inorganic substance that absorbs an aqueous liquid or a malodor to provide dampness and/or malodor control.

9. A process according to claim 8 wherein the inorganic substance is an absorbent clay.

10. A process according to claim 9 wherein the absorbent clay is selected from the group consisting of diatomaceous earth, Fuller's earth, bentonite, monmorillonite, kaolinite, hailosite, illite, Georgia Clay, and mixtures thereof.

11. A process according to claim 1 wherein the absorbent material is an organic substance that absorbs an aqueous liquid or a malodor to provide dampness and/or malodor control.

12. A process according to claim 11 wherein the organic substance is selected from the group consisting of ground corn cob, rice hull ash, ground alfalfa, wood shavings, chopped soya bean stalk, peanut hull, hulls of cereal grain, and mixtures thereof.

13. A process according to claim 1 wherein the absorbent material is a cellulosic substance that absorbs an aqueous liquid or a malodor to provide dampness and/or malodor control.

14. A process according to claim 13 wherein the cellulosic substance is selected from the group consisting of cellulose acetate, cellulose butyrate, cellulose proprionate, and mixtures thereof.

15. A process according to claim 1 wherein the absorbent material is a superabsorbent material that absorbs an aqueous liquid or a malodor to provide dampness and/or malodor control.

16. A process according to claim 15 wherein the superabsorbent material is a water swellable polymer.

17. A process according to claim 16 wherein the water swellable polymer is selected from the group consisting of polysaccharides, polyacrylates, polyacylonitriles, polyvinyl alcohol, hydrophilic polyurethanes, partially hydrolyzed polyacrylamides, sulphonated polystyrene, sulphonated polyethers, poly (alylene oxide), and mixtures thereof.

18. A process according to claim 1 wherein the delivery vehicle further comprises a deodorant.

19. A process according to claim 18 wherein the deodorant is selected from the group consisting of chlorophyll, sodium dihydrogen phosphate, potassium acid phthalate, sodium bicarbonate, and mixtures thereof.

20. A fragranced delivery vehicle in the form of a free flowing powder comprising a fragrance dispersed in a fixative, and an enrobement material, and wherein the said fragrance dispersed in the fixative is enrobed by the enrobement material.

21. A composition comprising the fragranced delivery vehicle according to claim 20 admixed with an absorbent material.

22. A fragranced delivery vehicle according to claim 20 wherein the ratio of fragrance to enrobement material is about 1:20 to about 2:5.

23. A fragranced delivery vehicle according to claim 22 wherein the ratio of fragrance to enrobement material is about 1:5.

24. A fragranced delivery vehicle according to claim 20 wherein the enrobement material is a clay, which is present at less than 50% (wt).

25. A fragranced delivery vehicle according to claim 24 wherein the clay is present at less than 15% (wt).

26. A composition for absorbing moisture and/or malodor and for imparting a fragrance to a surrounding environment comprising:
   from about 30% (wt) to about 98% (wt) of an absorbent material;
   from about 0% (wt) to 50% (wt) of fillers and binders; and,
   from about 1% (wt) to about 20% (wt) of a delivery vehicle, wherein the delivery vehicle is a free flowing powder which comprises, a fragrance dispersed in a fixative, the said fragrance dispersed in a fixative enrobed by an enrobement material.

27. A process for providing a fragrance and absorbing moisture and/or malodor to a substrate comprising:
   (a) providing a free flowing powder composition comprising a fragrance dispersed in a fixative, which fragrance dispersed in a fixative is enrobed by an enrobement material, and an absorbent material; and
   (b) contacting the free flowing powder with the substrate.

28. A process according to claim 27 wherein the substrate is selected from the group consisting of cat litter, air fresheners, sanitary products, and diapers.

29. A process according to claim 28 wherein the sanitary products are selected from the group consisting of catamenials, panty liners, adult incontinence pads, underarm shields, and shoe inserts.

30. A fragrancing and moisture and/or malodor suppression system comprising:
   (a) a free flowing powder comprising a fragrance dispersed in a fixative, which fragrance dispersed in a fixative is enrobed by an enrobement material, and, an absorbent material;
   (b) a housing means for housing the free flowing powder including the absorbent material; and
   (c) a vapor permeable outer material disposed about the housing means, wherein moisture and malodor from a surrounding environment may diffuse through the outer material and into the free flowing powder and fragrance from the free flowing powder may diffuse through the outer material into the surrounding environment.

31. A process for absorbing moisture and/or malodor, and providing a fragrance to the surrounding ambience consisting essentially of:
   (a) providing a delivery vehicle consisting essentially of an enrobement material, a fragrance, and a fixative, wherein the delivery vehicle is in the form of a free flowing powder, wherein the powder consists of a fragrance dispersed in a fixative, which fragrance dispersed in the fixative is enrobed by the enrobement material, wherein the enrobement material is selected from the group consisting of clays, silicas, celites, zeolites, metal salts, celluloses, starches, carbonates, borates, sulfates, water soluble polymers, borax, and mixtures thereof;
   (b) combining the delivery vehicle with an absorbent material to form a mixture; and (c) contacting the mixture of (a) and (b) with a moisture and/or a malodor source.

32. A process for absorbing moisture and/or malodor, and providing a fragrance to the surrounding ambience consisting of:
   (a) providing a delivery vehicle consisting essentially of an enrobement material, a fragrance, and a fixative, wherein the delivery vehicle is in the form of a free flowing powder, wherein the powder consists of a fragrance dispersed in a fixative, which fragrance dispersed in the fixative is enrobed by the enrobement material, wherein the enrobement material is selected from the group consisting of clays, silicas, celites, zeolites, metal salts, celluloses, starches, carbonates, borates, sulfates, water soluble polymers, borax, and mixtures thereof;
   (b) combining the delivery vehicle with an absorbent material to form a mixture; and (c) contacting the mixture of (a) and (b) with a moisture and/or a malodor source.

33. A process for absorbing moisture and/or malodor, and providing a fragrance to the surrounding ambience consisting of:
   (a) providing a delivery vehicle consisting of an enrobement material, a fragrance, and a fixative, wherein the delivery vehicle is in the form of a free flowing powder, wherein the powder consists of a fragrance dispersed in a fixative, which fragrance dispersed in the fixative is enrobed by the enrobement material, wherein the enrobement material is selected from the group consisting of clays, silicas, celites, zeolites, metal salts, celluloses, starches, carbonates, borates, sulfates, water soluble polymers, borax, and mixtures thereof;
   (b) combining the delivery vehicle with an absorbent material to form a mixture; and (c) contacting the mixture of (a) and (b) with a moisture and/or a malodor source.

34. A delivery vehicle, for absorbing moisture and/or malodor, and providing a fragrance to the surrounding ambience, comprising:
   an enrobement material, a fragrance, and a fixative, which is selected from the group consisting of polyethylene glycol, glycerol, mineral oil, and mixtures thereof;
   wherein the delivery vehicle is in the form of a free flowing powder, wherein the powder consists of a fragrance dispersed in the fixative, wherein the fragrance dispersed in the fixative is enrobed by the enrobement material, wherein the enrobement material is selected from the group consisting of clays, silicas, celites, zeolites, metal salts, celluloses, starches, carbonates, borates, sulfates, water soluble polymers, borax, and mixtures thereof.

* * * * *